(12) United States Patent
Shue et al.

(10) Patent No.: US 7,192,418 B2
(45) Date of Patent: Mar. 20, 2007

(54) DISPOSABLE SYRINGE

(76) Inventors: Ming-Jeng Shue, No. 14, Lane 8, Chung-I St., Hsi Dist., Taichung City (TW); Phillip Shue, No. 14, Lane 8, Chung-I St., Hsi Dist., Taichung City (TW)

( * ) Notice: Subject to any disclaimer, the term of this patent is extended or adjusted under 35 U.S.C. 154(b) by 0 days.

(21) Appl. No.: 10/288,351

(22) Filed: Nov. 4, 2002

(65) Prior Publication Data

US 2003/0212368 A1  Nov. 13, 2003

Related U.S. Application Data

(63) Continuation-in-part of application No. 10/143,461, filed on May 10, 2002, now Pat. No. 7,066,906.

(51) Int. Cl.
*A61M 5/32* (2006.01)

(52) U.S. Cl. .................. 604/195; 604/240; 604/110

(58) Field of Classification Search .......... 604/110, 604/164.08, 187, 192, 195–196, 198, 240, 604/243, 263; 128/919

See application file for complete search history.

(56) References Cited

U.S. PATENT DOCUMENTS 5,098,402 A * 3/1992 Davis .................... 604/195
5,112,315 A * 5/1992 Gloyer et al. ............ 604/195
5,205,824 A * 4/1993 Mazur .................... 604/110
5,342,308 A * 8/1994 Boschetti ................ 604/110
5,531,705 A * 7/1996 Alter et al. ............. 604/195
5,938,641 A * 8/1999 Villanueva ............. 604/195
5,976,895 A   11/1999 Cipkowski
5,976,896 A   11/1999 Kumar et al.
6,099,522 A    8/2000 Knopp et al.
6,196,997 B1 * 3/2001 Saito .................... 604/195
6,341,182 B1   1/2002 Fitzgerald et al.
6,376,251 B1   4/2002 Braun et al.

* cited by examiner

*Primary Examiner*—Catherine S. Williams
(74) *Attorney, Agent, or Firm*—Townsend and Townsend and Crew LLP

(57) ABSTRACT

A disposable syringe has a needle seat with an upper segment adapted to be fitted with a needle cannula, and a lower segment retained in a passage of a barrel. A plunger has a stem portion movable in the passage, a deformable surrounding engaging portion in sealing contact with the passage so as to be moved by the stem portion to a position of use, and a surrounding abutting head which is moved towards and which is held by a grip segment in the needle seat when the surrounding engaging portion is depressed by an edge portion of the needle seat by virtue of a continuing depression force of the plunger, thereby permitting the needle seat to be brought into the passage for disposal.

6 Claims, 6 Drawing Sheets

DISPOSABLE SYRINGE

CROSS-REFERENCE TO RELATED APPLICATION

This application is a continuation-in-part of U.S. patent application Ser. No. 10/143,461, filed by the applicant on May 10, 2002 now U.S. Pat. No. 7,066,906, the entire disclosure of which is incorporated herein by reference.

BACKGROUND OF THE INVENTION

1. Field of the Invention

This invention relates to a disposable syringe, more particularly to a disposable syringe which enables a needle cannula to be retracted within a barrel after use for safe disposal.

2. Description of the Related Art

In co-pending U.S. patent application Ser. No. 10/143,461, the applicant disclosed a disposable syringe that includes a barrel, a tubular needle seat, and a plunger. The barrel has an inner surrounding barrel wall surface which confines a passage and which includes a larger-diameter segment and a smaller-diameter segment that are disposed proximate to lower and upper open ends, respectively, so as to confine a surrounding shoulder portion therebetween. The tubular needle seat is insertable into the passage, and includes a lower surrounding edge portion which abuts against the surrounding shoulder portion, and a surrounding seat wall which has an inner tubular wall surface that has a grip segment, and an outer tubular wall surface that includes a lower segment retained at the smaller-diameter segment by virtue of a first friction force, and an upper segment adapted to be sleeved over by a needle hub of a needle unit. The plunger includes a stem portion which is movable in the passage of the barrel and which has an outer segment that extends outwardly of the lower open end of the barrel, a surrounding engaging portion which is retainingly sleeved on an inner segment of the stem portion by virtue of a second friction force and which is in sealing contact with and which is slidable relative to the larger-diameter segment so as to be moved with the stem portion, and a head which extends from the inner segment toward the grip segment. As such, when the surrounding engaging portion is brought by the inner segment to engage the lower surrounding edge portion, and is depressed by the lower surrounding edge portion against the second friction force by a manual force which is generated as a consequence of continuing movement of the inner segment, the surrounding engaging portion is retained by the lower surrounding edge portion to thereby permit the head to move towards the grip segment of the tubular needle seat and to be held by virtue of a fourth friction force that is greater than the first friction force. Therefore, the used needle unit can be enclosed in the passage of the barrel for safe disposal.

It is desirable to improve the aforesaid disposable syringe to simplify the construction thereof and to be adapted for use in conjunction with needle units of various forms.

SUMMARY OF THE INVENTION

The object of the present invention is to provide a disposable syringe which has a simpler construction and which is adapted to be used in conjunction with needle units of various forms.

According to this invention, the disposable syringe includes a barrel having an inner surrounding barrel wall surface which surrounds an axis and which confines a passage. The passage has lower and upper open ends disposed opposite to each other in a longitudinal direction parallel to the axis. The inner surrounding barrel wall surface includes a larger-diameter segment and a smaller-diameter segment which are disposed proximate to the lower and upper open ends, respectively, and which cooperatively form a surrounding shoulder portion therebetween.

A tubular needle seat is insertable into the passage from the lower open end toward the upper open end, and includes a lower surrounding edge portion disposed to abut against the first surrounding shoulder portion, an upper surrounding edge portion disposed opposite to the lower surrounding edge portion in the longitudinal direction, and a surrounding seat wall interposed therebetween. The surrounding seat wall has an inner tubular wall surface which surrounds the axis to confine a duct, which forms a grip segment, and which is adapted to be fitted with a needle cannula, and an outer tubular wall surface. The outer tubular wall surface includes a lower segment proximate to the lower surrounding edge portion, and an upper segment disposed opposite to the lower segment and proximate to the upper surrounding edge portion. The tubular needle seat is inserted into the passage. Thus, the lower segment engages and is retained at the smaller-diameter segment, and the lower surrounding edge portion abuts against the surrounding shoulder portion.

A plunger includes a stem portion which is disposed to be movable in the passage and which has inner and outer segments opposite to each other in the longitudinal direction. The outer segment extends outwardly of the lower open end of the passage. An actuated end extends from the outer segment so as to be actuated to move the stem portion along the passage. A surrounding engaging portion is retainingly sleeved on the inner segment by virtue of a second friction force, and is in sealing contact with and is slidable relative to the larger-diameter segment so as to be moved with the stem portion to the position of use. A head extends from the inner segment toward the grip segment.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
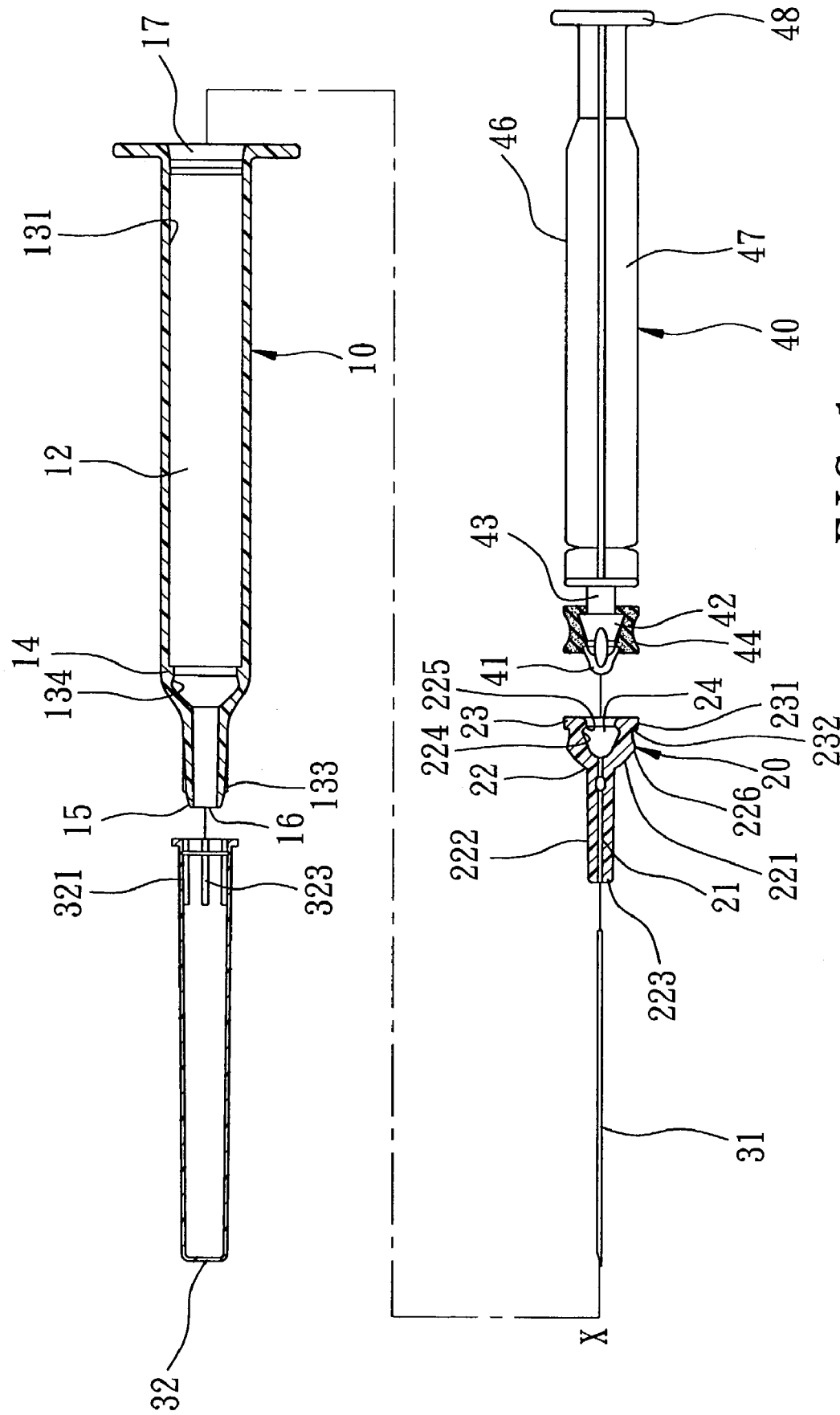
FIG. 1 is an exploded longitudinal sectional view showing a first preferred embodiment of a disposable syringe according to this invention for use with a needle cannula to form a syringe assembly.

Before the present invention is described in greater detail, it should be noted that same reference numerals have been used to denote like elements throughout the specification.

Figure 2:
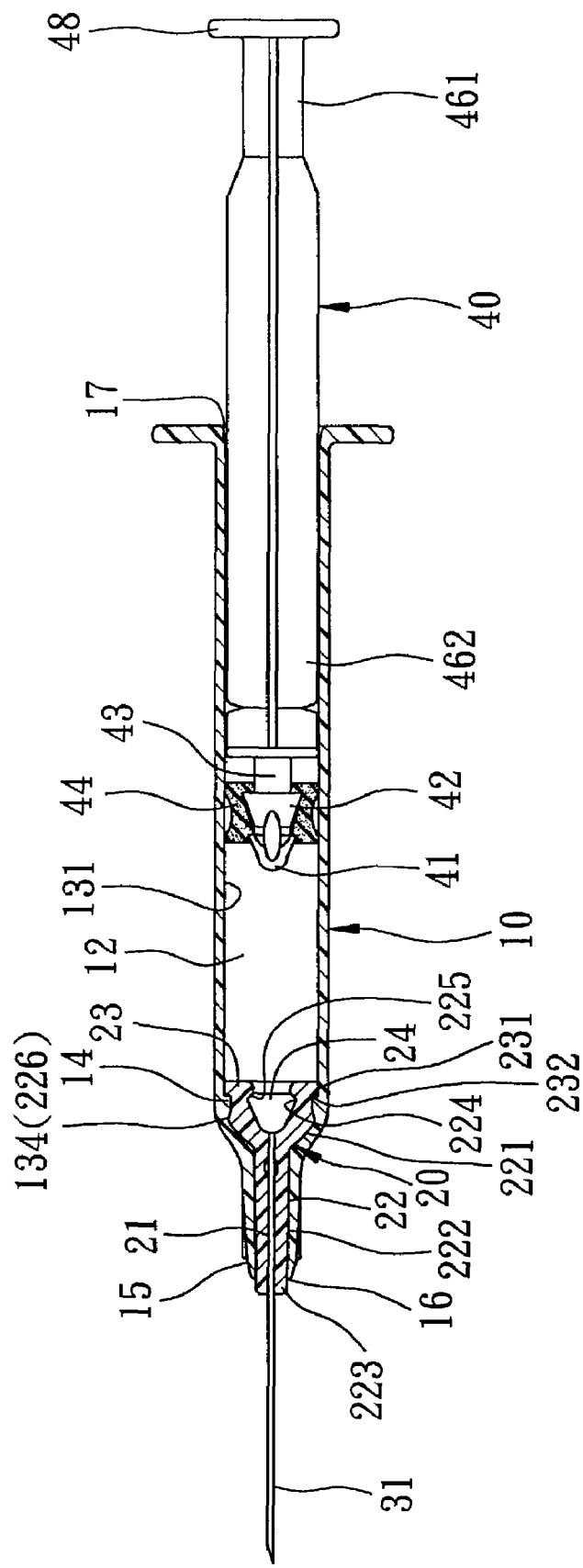
FIG. 2 is a longitudinal sectional view showing the syringe assembly during use.
Figure 3:
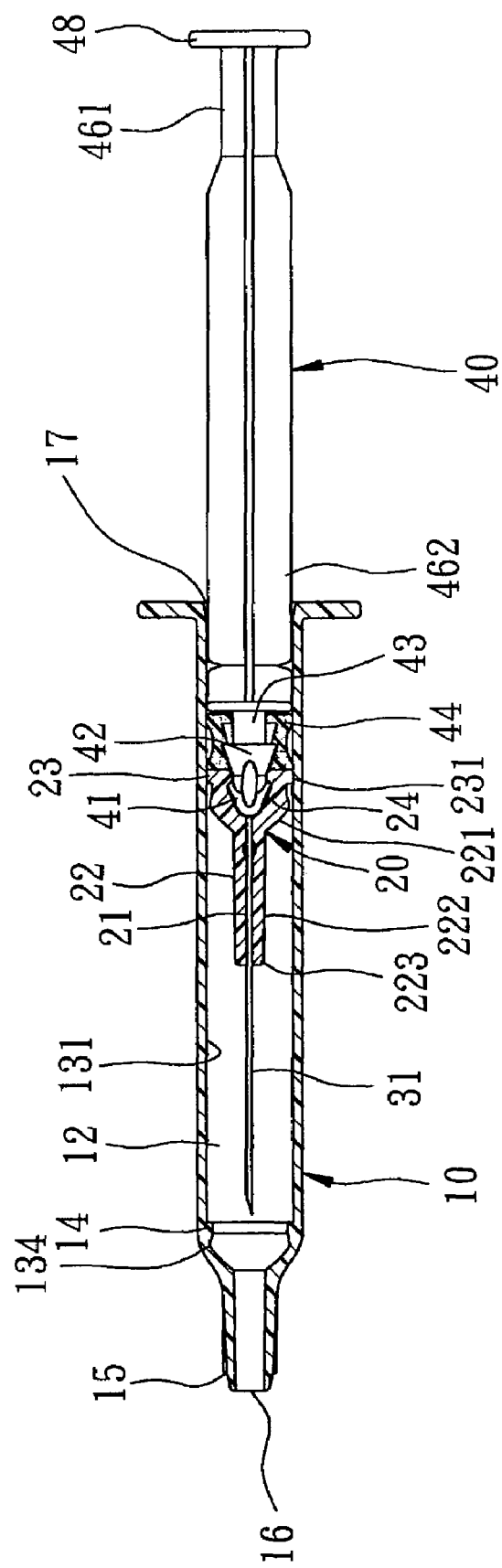
FIG. 3 is a longitudinal sectional view showing the syringe assembly in a retracted state.

Referring to FIGS. 1, 2 and 3, the first preferred embodiment of the disposable syringe according to the present invention is shown to be used with a needle cannula 31 to form a syringe assembly.

The syringe in this embodiment is shown to comprise a barrel 10, a tubular needle seat 20, and a plunger 40.

The barrel 10 has an inner surrounding barrel wall surface which surrounds an axis (X) and which confines a passage 12. The passage 12 has lower and upper open ends 17, 16 which are disposed opposite to each other in a longitudinal direction that is parallel to the axis (X). The inner surrounding barrel wall surface includes a larger-diameter segment 131 and a smaller-diameter segment 134 which are disposed proximate to the lower and upper open ends 17, 16, respectively, and which cooperatively form a first surrounding shoulder portion 14 therebetween.

The barrel 10 further has an outer surrounding wall surface which is disposed opposite to the inner surrounding barrel wall surface in radial directions, and which has a sleeved portion 15 that is disposed proximate to the upper open end 16 and that is formed with a plurality of friction ribs 133. A tip protector 32 has an internal sleeve end 321 which is configured to be sleeved on the sleeved portion 15 for shielding the needle cannula 31, and which has a plurality of longitudinally extending friction ribs 323 for engaging the friction ribs 133.

The tubular needle seat 20 is disposed to be insertable into the passage 12 from the lower open end 17 toward the upper open end 16. The needle seat 20 includes a lower surrounding edge portion 23 disposed to abut against the first surrounding shoulder portion 14 and having an outer surrounding surface 231 which abuts sealingly against the larger-diameter segment 131, an upper surrounding edge portion 223 disposed opposite to the lower surrounding edge portion 23 in the longitudinal direction, and a surrounding seat wall 22 interposed therebetween.

The seat wall 22 has an inner tubular wall surface 21 which surrounds the axis (X) to confine a duct 24. The inner tubular wall surface 21 has a narrow upper segment which is adapted to be fitted with the needle cannula 31, and an enlarged lower segment which forms a grip segment. In this embodiment, the grip segment includes a concave portion 224 which extends inwardly from the inner tubular wall surface 21 in radial directions relative to the axis (X) to form a second surrounding shoulder portion 225 that is adjacent to the lower surrounding edge portion 23.

The seat wall 22 further has an outer tubular wall surface which includes lower and upper segments 221, 222. The lower segment 221 is proximate to the lower surrounding edge portion 23, and has a retaining protrusion 226 formed thereon. When the upper surrounding edge portion 223 is forced to extend outwardly of the upper open end 16 of the barrel 10 after the tubular needle seat 20 is inserted into the passage 12, the lower segment 221 will be brought to a position of use, as shown in FIG. 2, where the lower segment 221 engages and is retained at the smaller-diameter segment 134 by virtue of a first friction force which is generated as a result of retaining engagement between the retaining protrusion 226 and the smaller-diameter segment 134 when an upper edge surface 232 of the lower surrounding edge portion 23 abuts against the first surrounding shoulder portion 14 of the barrel 10. The upper segment 222 is disposed opposite to the lower segment 221 and proximate to the upper surrounding edge portion 223.

The plunger 40 includes a stem portion 46 which is movable in the passage 12 of the barrel 10. The stem portion 46 has a plurality of wing plates 47, a connecting shank 43 extending from upper edges of the wing plates 47, and a retaining protrusion 42. On the other hand, as shown in FIG. 2, the stem portion 46 includes inner and outer segments 462, 461 opposite to each other in the longitudinal direction. The outer segment 461 extends outwardly of the lower open end 17 of the barrel 10. An actuated end 48, which is a thumb rest, extends from the outer segment 461 so as to be actuated to move the stem portion 47 along the passage 12.

The plunger 40 further includes a tapered surrounding abutting head 41 which extends from the retaining protrusion 42 of the inner segment 462 toward the grip segment of the needle seat 20. Moreover, the surrounding abutting head 41 and the retaining protrusion 42 are configured to be substantially hollow so as to provide greater flexibility.

A deformable surrounding engaging portion 44, preferably made of an elastic material, is retainingly sleeved on the entire retaining protrusion 42 of the inner segment 462 and a portion of the surrounding abutting head 41 to generate a second friction force. An outer surrounding surface of the surrounding engaging portion 44 sealingly contacts, and is slidable relative to the larger-diameter segment 131 of the barrel 10 so as to be moved with the stem portion 46.

In use, the plunger 40 is pressed forwardly to push the surrounding engaging portion 44 to abut against the lower surrounding edge portion 23 of the needle seat 20. Since the surrounding abutting head 41 is configured to be fitted in the enlarged lower segment of the inner tubular wall surface 21, drug solution in the passage 12 can be almost completely injected through the needle cannula 31.

Subsequently, referring to FIG. 3, when the plunger 40 is further moved forward by a third force towards the smaller-diameter segment 134 against the second friction force between the inner segment 462 and the surrounding engaging portion 44, the surrounding engaging portion 44 is deformed by the lower surrounding edge portion 23, thereby permitting the surrounding abutting head 41 to move in the concave portion 224 of the needle seat 20 to abut against the second surrounding shoulder portion 225 so as to form a fourth friction force that is greater than the first friction force between the retaining protrusion 226 and the smaller-diameter segment 134. Then, the outer segment 461 of the plunger 40 is pulled backward to be remote from the lower open end 17 so that the needle seat 20, on which the used needle cannula 31 is mounted, is retracted into the passage 12 through the upper open end 16 to bring the upper surrounding edge portion 223 to a retracted position. In this state, the used needle cannula 31 can be enclosed in the passage 12 of the barrel 20 for safe disposal.

In the syringe assembly of this invention, the number of components is decreased since a needle hub is eliminated.

Figure 4:
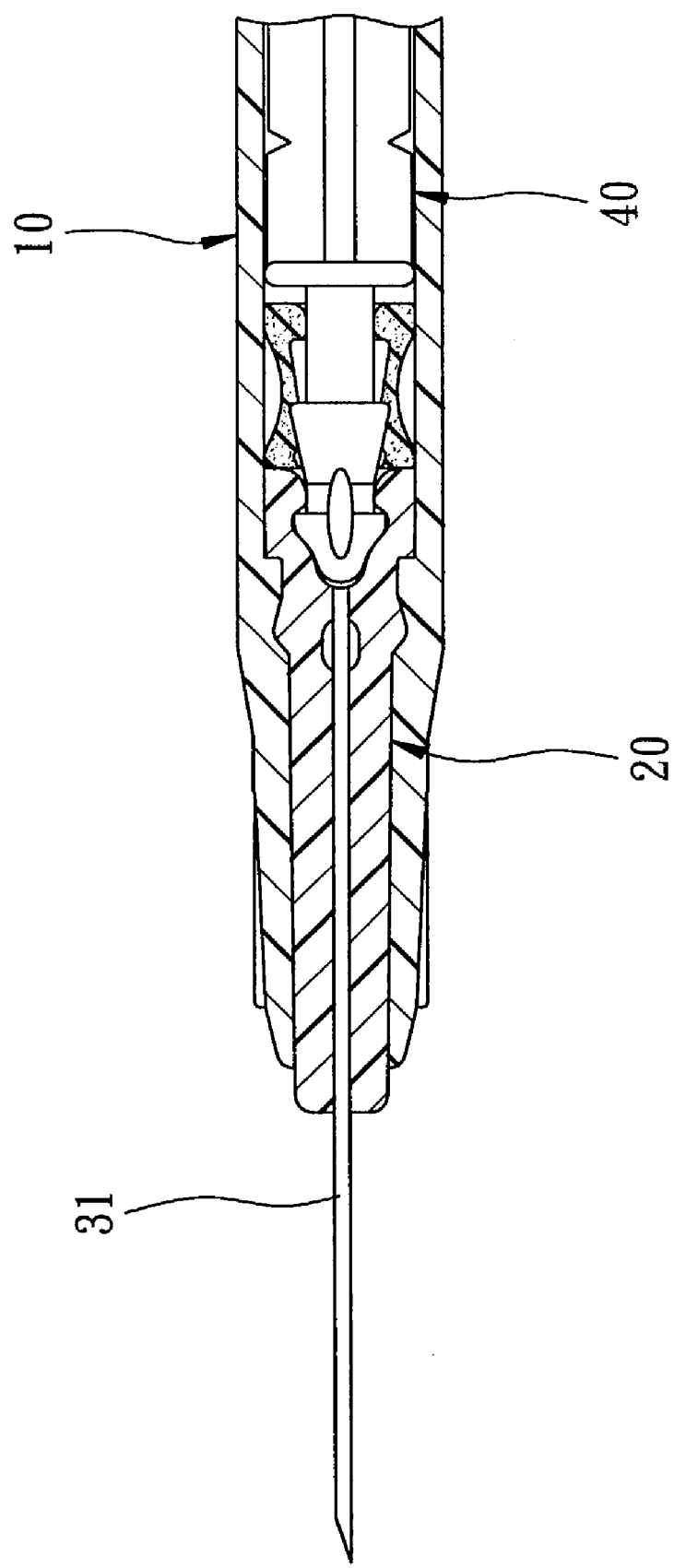
FIG. 4 is a fragmentary longitudinal sectional view showing a second preferred embodiment of a disposable syringe according to this invention for use with a needle cannula.

Referring to FIG. 4, the second preferred embodiment of the disposable syringe is similar to the first preferred embodiment in construction, and is used for an extremely small injection volume, such as 1 ml. Thus, the dimensions of the barrel 10, the needle seat 20, the needle cannula 31 and the plunger 40 are smaller than those of the aforesaid embodiment.

Figure 5:
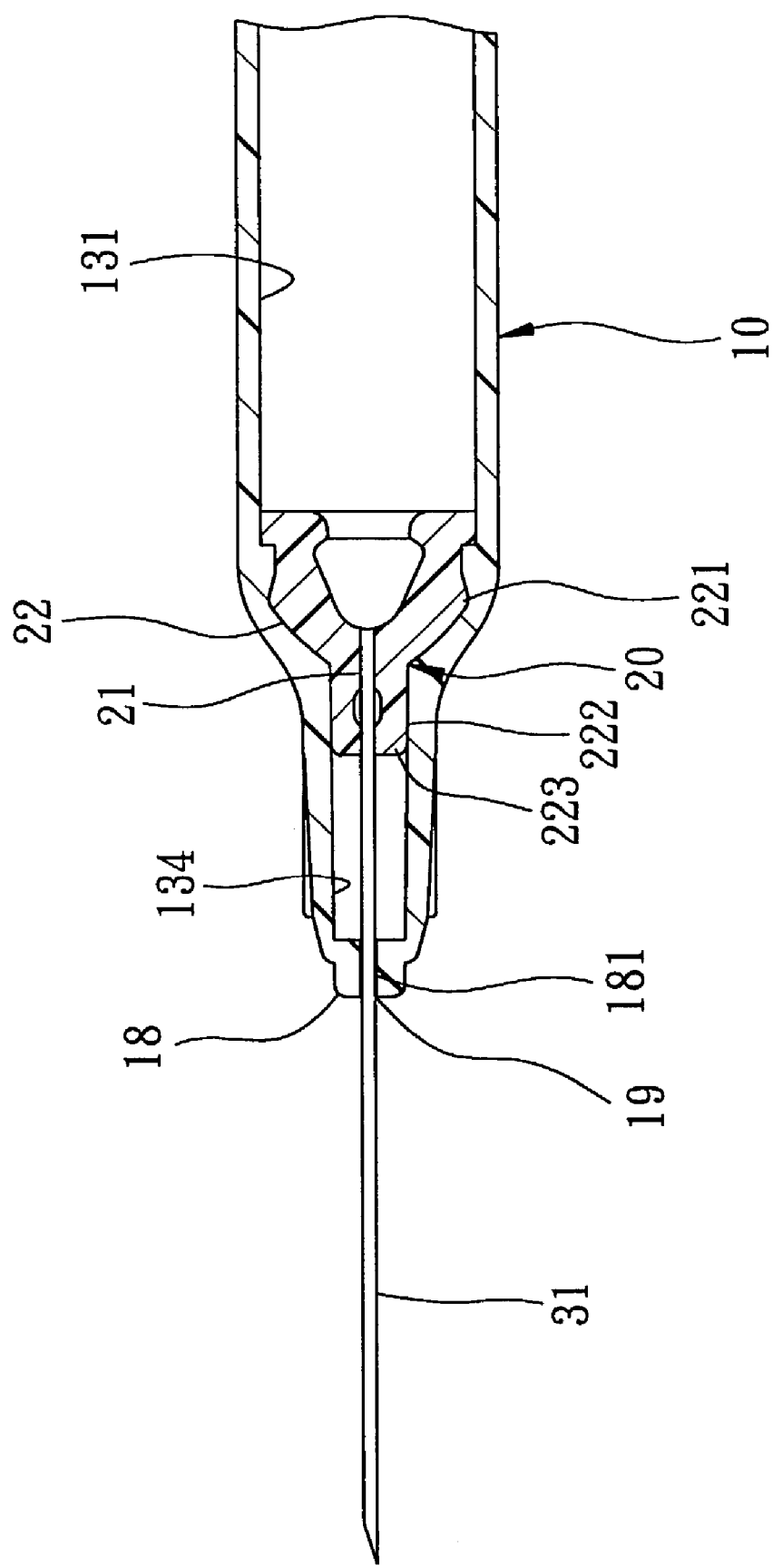
FIG. 5 is a fragmentary longitudinal sectional view showing a third preferred embodiment of a disposable syringe according to this invention for use with a needle cannula.
Figure 6:
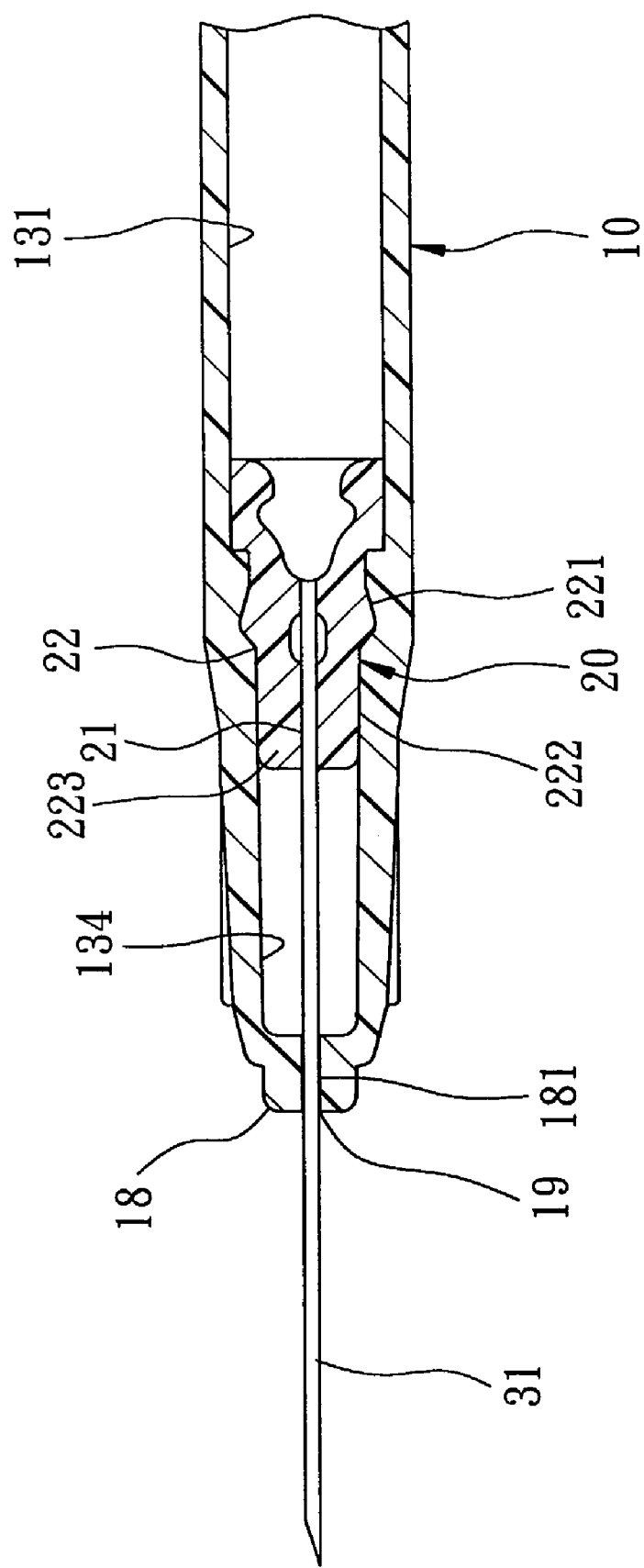
FIG. 6 is a fragmentary longitudinal sectional view showing a fourth preferred embodiment of a disposable syringe according to this invention for use with a needle cannula.

Referring to FIGS. 5 and 6, the third and fourth preferred embodiments of the disposable syringe according to this invention are shown to be respectively similar to the first and second embodiments in construction. The differences therebetween reside in that the upper surrounding edge portion 223 is retained in the smaller-diameter segment 134 of the barrel 10 in the position of use, and the upper open end 18 of the barrel 10 has a surrounding edge wall 181 which extends from the smaller-diameter segment 134 toward the axis (X) and which confines a through hole 19 that surrounds the axis (X). As such, the needle cannula 31 can pass through the through hole 19 and outwardly of the upper open end 18. The fourth preferred embodiment shown in FIG. 6 is similar to the third preferred embodiment in construction, but is used for an extremely small injection volume, such as 1 ml.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

We claim:

1. A disposable syringe adapted to be used with a needle cannula, comprising:
    a barrel having an inner surrounding barrel wall surface which surrounds an axis and which confines a passage, said passage having lower and upper open ends which are disposed opposite to each other in a longitudinal direction that is parallel to the axis, said inner surrounding barrel wall surface including a larger-diameter segment and a smaller-diameter segment which are disposed proximate to said lower and upper open ends, respectively, and which cooperatively form a first surrounding shoulder portion therebetween;
    a tubular needle seat disposed to be insertable into said passage from said lower open end toward said upper open end, said needle seat including
    a lower surrounding edge portion which is disposed to abut against said first surrounding shoulder portion,
    an upper surrounding edge portion disposed opposite to said lower surrounding edge portion in the longitudinal direction, and
    a surrounding seat wall interposed between said lower and upper surrounding edge portions, and having an inner tubular wall surface which surrounds the axis to confine a duct, which has a grip segment, and which is adapted to be fitted with the needle cannula, and an outer tubular wall surface which includes
    a lower segment proximate to said lower surrounding edge portion, and configured such that, when said upper surrounding edge portion is forced to extend toward said upper open end after said tubular needle seat is inserted into said passage, said lower segment will be brought to a position of use, where said lower segment engages and is retained at said smaller-diameter segment by virtue of a first friction force which is generated between the lower segment and the smaller-diameter segment when said lower surrounding edge portion abuts against said first surrounding shoulder portion, and such that, when said upper surrounding edge portion is moved against the first friction force toward said lower open end passing said large-diameter segment, said needle seat will be brought to a retracted position, where said lower segment and said lower surrounding edge portion are remote from said smaller-diameter segment and said first surrounding shoulder portion, respectively, and
    an upper segment disposed opposite to said lower segment and proximate to said upper surrounding edge portion; and
    a plunger including
    a stem portion disposed to be movable in said passage of said barrel, and having inner and outer segments opposite to each other in the longitudinal direction, said outer segment extending outwardly of said lower open end,
    an actuated end extending from said outer segment so as to be actuated to move said stem portion along said passage,
    a surrounding engaging portion which is disposed to retainingly sleeve on said inner segment by virtue of a second friction force, and which is in sealing contact with and which is slidable relative to said larger-diameter segment so as to be moved with said stem portion to the position of use, and
    a head disposed to extend from said inner segment toward said grip segment of said inner tubular wall surface, and configured such that, when said surrounding engaging portion is brought by said inner segment to engage said lower surrounding edge portion and is depressed by said lower surrounding edge portion by virtue of a third force which is generated as a consequence of continuing movement of said inner segment towards said smaller-diameter segment, the third force being greater than the second friction force, said surrounding engaging portion is retained by said lower surrounding edge portion to thereby permit said head to move towards said grip segment and to be held by virtue of a fourth friction force that is greater than the first friction force while said lower segment remains engaged and unmoved relative to said smaller-diameter segment.

2. The disposable syringe of claim 1, wherein said barrel has an outer surrounding wall surface disposed opposite to said inner surrounding barrel wall surface in radial directions, and having a sleeved portion which is disposed proximate to said upper open end, said disposable syringe further comprising a tip protector which has an internal sleeve end configured to be sleeved on said sleeved portion so as to shield the needle cannula.

3. The disposable syringe of claim 2, wherein each of said sleeved portion and said internal sleeve end has a plurality affliction ribs formed thereon.

4. The disposable syringe of claim 3, wherein said upper open end has a surrounding edge wall which extends from said smaller-diameter segment of said inner surrounding barrel wall surface toward the axis and which confines a through hole that surrounds the axis and that is adapted for passage of the needle cannula.

5. The disposable syringe of claim 1, wherein the fourth friction force is generated when the lower surrounding edge portion is linearly moved towards said lower open end.

6. The disposable syringe of claim 1, wherein the third force is generated as a consequence of a continuing linear movement of said inner segment towards said smaller-diameter segment.

* * * * *